(12) United States Patent
Bortolin et al.

(10) Patent No.: US 11,478,651 B2
(45) Date of Patent: Oct. 25, 2022

(54) SYSTEMS AND METHODS FOR MANUFACTURING HEADER SUBASSEMBLY

(71) Applicant: PACESETTER, INC., Sylmar, CA (US)

(72) Inventors: Dino Bortolin, Camarillo, CA (US); Ofer Rosenzweig, Chatsworth, CA (US)

(73) Assignee: PACESETTER, INC., Sylmar (CA)

( * ) Notice: Subject to any disclaimer, the term of this patent is extended or adjusted under 35 U.S.C. 154(b) by 266 days.

(21) Appl. No.: 16/941,864

(22) Filed: Jul. 29, 2020

(65) Prior Publication Data

US 2020/0353267 A1 Nov. 12, 2020

Related U.S. Application Data

(62) Division of application No. 15/956,544, filed on Apr. 18, 2018, now Pat. No. 10,765,874, which is a
(Continued)

(51) Int. Cl.
*A61N 1/375* (2006.01)
*A61N 1/05* (2006.01)
(Continued)

(52) U.S. Cl.
CPC ......... *A61N 1/3752* (2013.01); *A61N 1/0534* (2013.01); *A61N 1/362* (2013.01); *A61N 1/36067* (2013.01); *A61N 1/37229* (2013.01); *B29C 43/18* (2013.01); *B29C 45/14819* (2013.01); *B29C 65/18* (2013.01); *B29C 65/20* (2013.01); *B29C 65/7814* (2013.01); *B29C 66/1122* (2013.01); *B29C 66/54* (2013.01); *B29C 66/73921* (2013.01); *B29C 66/73941* (2013.01); *B29C 66/742* (2013.01); *B29C 66/8322* (2013.01); *B29C 66/9141* (2013.01); *B29C 66/9241* (2013.01); *B29C 43/52* (2013.01); *B29C 66/71* (2013.01);
(Continued)

(58) Field of Classification Search
None
See application file for complete search history.

(56) References Cited

U.S. PATENT DOCUMENTS 7,212,110 B1    5/2007  Martin et al.
7,228,179 B2    6/2007  Campen et al.
(Continued)

FOREIGN PATENT DOCUMENTS

WO    2001093953 A1    12/2001

*Primary Examiner* — Michael W Kahelin
(74) *Attorney, Agent, or Firm* — Armstrong Teasdale LLP (57) ABSTRACT

The present disclosure provides systems and methods for assembling a subassembly for use in manufacturing an implantable device header. A method includes placing a first split web into a top platen, placing a second split web into a bottom platen, placing a conductor assembly and an antenna assembly in the bottom platen on top of the second split web, compressing the top and bottom platens together, heating the top and bottom platens until a predetermined temperature and a predetermined pressure are reached, such that first split web is fused to the second split web to form the subassembly, separating the top and bottom platens, and removing the formed subassembly.

6 Claims, 7 Drawing Sheets

Related U.S. Application Data division of application No. 14/969,634, filed on Dec. 15, 2015, now Pat. No. 9,974,966.

(51) Int. Cl.

| | |
|---|---|
| A61N 1/36 | (2006.01) |
| A61N 1/362 | (2006.01) |
| A61N 1/372 | (2006.01) |
| B29C 65/20 | (2006.01) |
| B29C 43/18 | (2006.01) |
| B29C 45/14 | (2006.01) |
| B29C 65/18 | (2006.01) |
| B29C 65/78 | (2006.01) |
| B29C 65/00 | (2006.01) |
| B29K 701/12 | (2006.01) |
| B29K 701/10 | (2006.01) |
| B29K 663/00 | (2006.01) |
| B29L 31/00 | (2006.01) |
| B29L 31/34 | (2006.01) |
| B29C 43/52 | (2006.01) |

(52) U.S. Cl.
CPC .... *B29C 2043/189* (2013.01); *B29K 2663/00* (2013.01); *B29K 2701/10* (2013.01); *B29K 2701/12* (2013.01); *B29L 2031/3456* (2013.01); *B29L 2031/3481* (2013.01); *B29L 2031/753* (2013.01)

(56) References Cited

U.S. PATENT DOCUMENTS

| | | | |
|---|---|---|---|
| 7,571,007 B2 | 8/2009 | Erickson et al. | |
| 7,955,543 B2* | 6/2011 | Deininger | A61N 1/375 |
| | | | 264/279.1 |
| 8,103,348 B1* | 1/2012 | Coffed | A61N 1/3752 |
| | | | 607/37 |
| 9,480,849 B2* | 11/2016 | Nolan | A61N 1/37512 |
| 9,795,796 B2 | 10/2017 | Bortolin et al. | |
| 10,420,949 B2 | 9/2019 | Seitz et al. | |
| 2006/0170486 A1 | 8/2006 | Tranchina et al. | |

\* cited by examiner

SYSTEMS AND METHODS FOR MANUFACTURING HEADER SUBASSEMBLY

CROSS REFERENCE TO RELATED APPLICATIONS

This is a divisional of U.S. patent application Ser. No. 15/956,544, which was filed on Apr. 18, 2018, and which is a divisional of U.S. patent application Ser. No. 14/969,634, which was filed on Dec. 15, 2015, and which has now issued as U.S. Pat. No. 9,974,966, all of which are herein incorporated by reference.

FIELD OF THE DISCLOSURE

The present disclosure relates generally to neurostimulation systems, and more particularly to manufacturing a header subassembly for an implantable pulse generator.

BACKGROUND ART

Parkinson's disease (PD) is a neurogenerative disorder that is characterized by pathological rhythmic neuronal oscillations that lead to symptoms such as tremor and bradykinesia. Deep brain stimulation (DBS) systems may be used to apply stimulation to provide symptom relief. For example, for PD, stimulation may be applied to a region in the basal ganglia, such as the subthalamic nucleus or global pallidus internus. In at least some known DBS devices, stimulation is applied using a train of individual pulses at a fixed frequency and pulse width.

At least some known DBS devices (and other stimulation devices) include an implantable pulse generator (IPG) and at least one stimulation lead coupled to the IPG. The IPG includes a header that includes conductors for making electrical connections to the at least one stimulation lead. The header may also include an antenna that facilitates communication between the IPG and an external device (e.g., a patient or clinician programmer). When manufacturing the header, to ensure proper functionality of the IPG, required spacing between internal electrical conductors (e.g., wires, ribbons, antennas, blocks, rings, etc.) must be maintained. However, this may be difficult using at least some known manufacturing methods.

BRIEF SUMMARY OF THE DISCLOSURE

In one embodiment, the present disclosure is directed to a method for assembling a subassembly for use in manufacturing an implantable device header. The method includes placing a first split web into a top platen, placing a second split web into a bottom platen, placing a conductor assembly and an antenna assembly in the bottom platen on top of the second split web, compressing the top and bottom platens together, heating the top and bottom platens until a predetermined temperature and a predetermined pressure are reached, such that first split web is fused to the second split web to form the subassembly, separating the top and bottom platens, and removing the formed subassembly.

In another embodiment, the present disclosure is directed to a system for assembling a subassembly for use in manufacturing an implantable device header. The system includes a first split web, a second split web, a conductor assembly, an antenna assembly, a top platen configured to receive the first split web, and a bottom platen configured to receive the second split web, the conductor assembly, and the antenna assembly such that the second split web is positioned below the conductor assembly and the antenna assembly, wherein to form the subassembly, the top and bottom platens are configured to compress together and increase in temperature to fuse the first split web to the second split web.

In another embodiment, the present disclosure is directed to an implantable device. The implantable device includes a header configured to electrically couple the implantable device to a stimulation lead, the header including a subassembly including a web assembly comprising a first split web fused to a second split web, a conductor assembly at least partially encapsulated by and positioned between the first split web and the second split web, and an antenna assembly at least partially encapsulated by and positioned between the first split web and the second split web.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for assembling a subassembly that may be used to manufacture a header for an implantable device. The subassembly includes a web assembly formed from a first split web and a second split web. For form the web assembly the first and second split webs are fused together while a conductor assembly and an antenna assembly are positioned between the first and second split webs. Accordingly, in the assembled subassembly, the fused first and second split webs facilitate securing a position and orientation of the conductor assembly and the antenna assembly.

Neurostimulation systems are devices that generate electrical pulses and deliver the pulses to nerve tissue of a patient to treat a variety of disorders. One category of neurostimulation systems is deep brain stimulation (DBS). In DBS, electrical pulses are delivered to parts of a subject's brain, for example, for the treatment of movement and effective disorders such as PD and essential tremor.

Neurostimulation systems generally include a pulse generator and one or more leads. A stimulation lead includes a lead body of insulative material that encloses wire conductors. The distal end of the stimulation lead includes multiple electrodes, or contacts, that are electrically coupled to the wire conductors. The proximal end of the lead body includes multiple terminals (also electrically coupled to the wire conductors) that are adapted to receive electrical pulses. In DBS systems, the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted within a subcutaneous pocket created during the implantation procedure.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Figure 1:
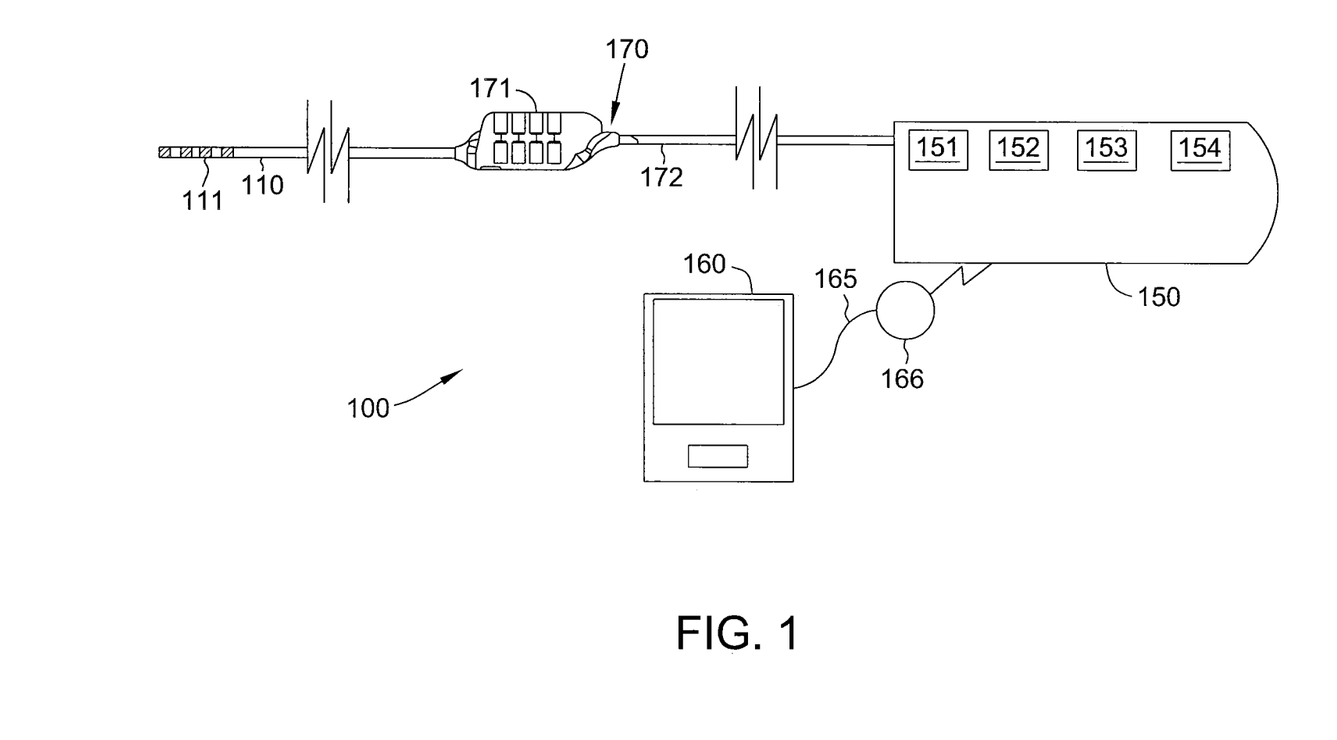
FIG. 1 is a schematic view of one embodiment of a stimulation system.

Referring now to the drawings and in particular to FIG. 1, a stimulation system is indicated generally at 100. Stimulation system 100 generates electrical pulses for application to tissue of a patient, or subject, according to one embodiment. Simulation system 100 includes an implantable pulse generator 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of implantable pulse generator 150 for execution by the microcontroller or processor to control the various components of the device.

Implantable pulse generator 150 may comprise one or more attached extension components 170 or be connected to one or more separate extension components 170. Alternatively, one or more stimulation leads 110 may be connected directly to implantable pulse generator 150. Within implantable pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from implantable pulse generator 150 and conducted through the conductors of lead body 172 are provided to stimulation lead 110. The pulses are then conducted through the conductors of stimulation lead 110 and applied to tissue of a patient via electrodes 111. Any suitable known or later developed design may be employed for connector portion 171.

For implementation of the components within implantable pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 150. Stimulation lead(s) 110 may include a lead body of insulative material about a plurality of conductors within the material that extend from a proximal end of stimulation lead 110 to its distal end. The conductors electrically couple a plurality of electrodes 111 to a plurality of terminals (not shown) of stimulation lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of implantable pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

Controller device 160 is also a device that permits the operations of implantable pulse generator 150 to be controlled by user after implantable pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with implantable pulse generator 150.

Controller device 160 preferably provides one or more user interfaces to allow the user to operate implantable pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from St. Jude Medical, Inc. (Plano, Tex.).

Figure 2:
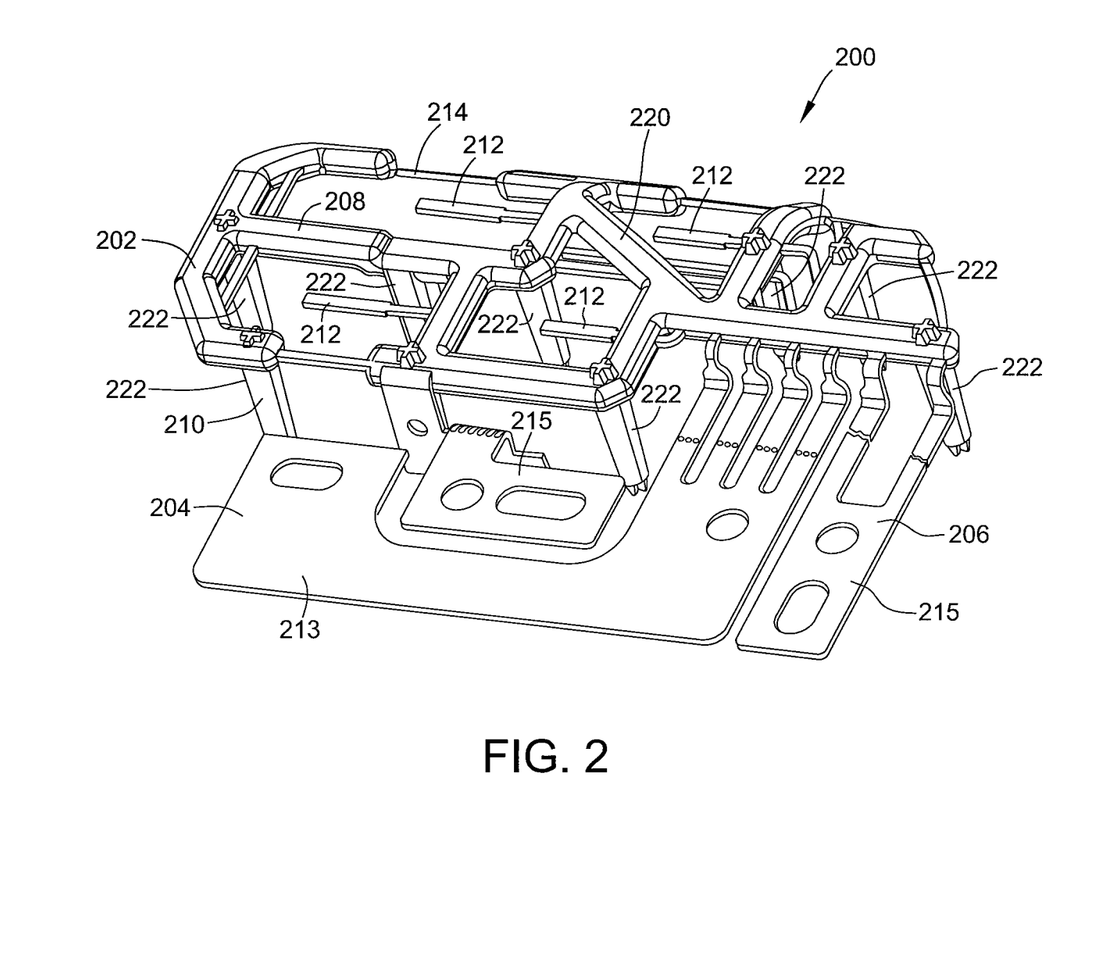
FIG. 2 is a perspective view of one embodiment of a subassembly that may be used in a header of an implantable pulse generator.

FIG. 2 is a perspective view of one embodiment of a subassembly 200 that may be used in a header of an implantable device, such as implantable pulse generator 150. Notably, subassembly 200 may be used in a header of any suitable implantable device, including, but not limited to, an IPG for a DBS system, a pacemaker, a defibrillator, a neuromodulator, and an implantable cardiac monitor.

Subassembly 200 includes a web assembly 202, a conductor assembly 204, and an antenna assembly 206. In this embodiment, web assembly 202 includes a first split web 208 and a second split web 210. To form subassembly 200, conductor assembly 204 and antenna assembly 206 are sandwiched between first and second split webs 208 and 210, as described herein.

Web assembly 202 facilitates supporting and maintaining a position of conductor assembly 204 and antenna assembly 206. As shown in FIG. 2, conductor assembly 204 includes a plurality of electrical conductors 212 and a conductor base plate 213. Further, antenna assembly 206 includes an antenna 214 that facilitates communications between the IPG and, for example, controller device 160 (shown in FIG. 1). Electrical conductors 212 and antenna 214 may have any suitable shape (e.g., flat ribbons, round wires, etc.). Antenna assembly 206 also includes two antenna base plates 215. Conductor and antenna base plates 213 and 215 may be used, for example, as electrical connections in the complete IPG header.

In this embodiment, web assembly 202 includes a web 220 and a plurality of struts 222 that extend substantially perpendicular to web 220. Notably, the shape and orientation of web assembly 202, conductor assembly 204, and antenna assembly 206 are merely examples. In other embodiments, web assembly 202, conductor assembly 204, and/or antenna assembly 206 may have any suitable shape or orientation.

Figure 3:
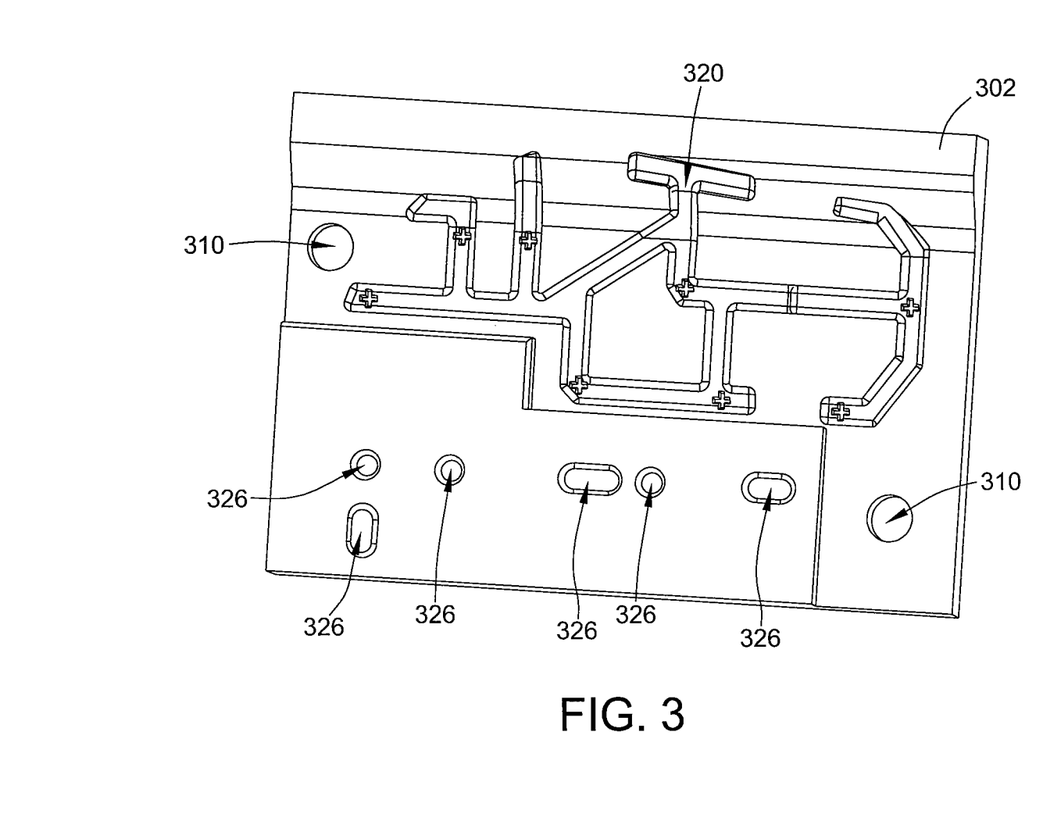
FIG. 3 is a perspective view of a top platen that may be used to form the subassembly shown in FIG. 2.
Figure 4:
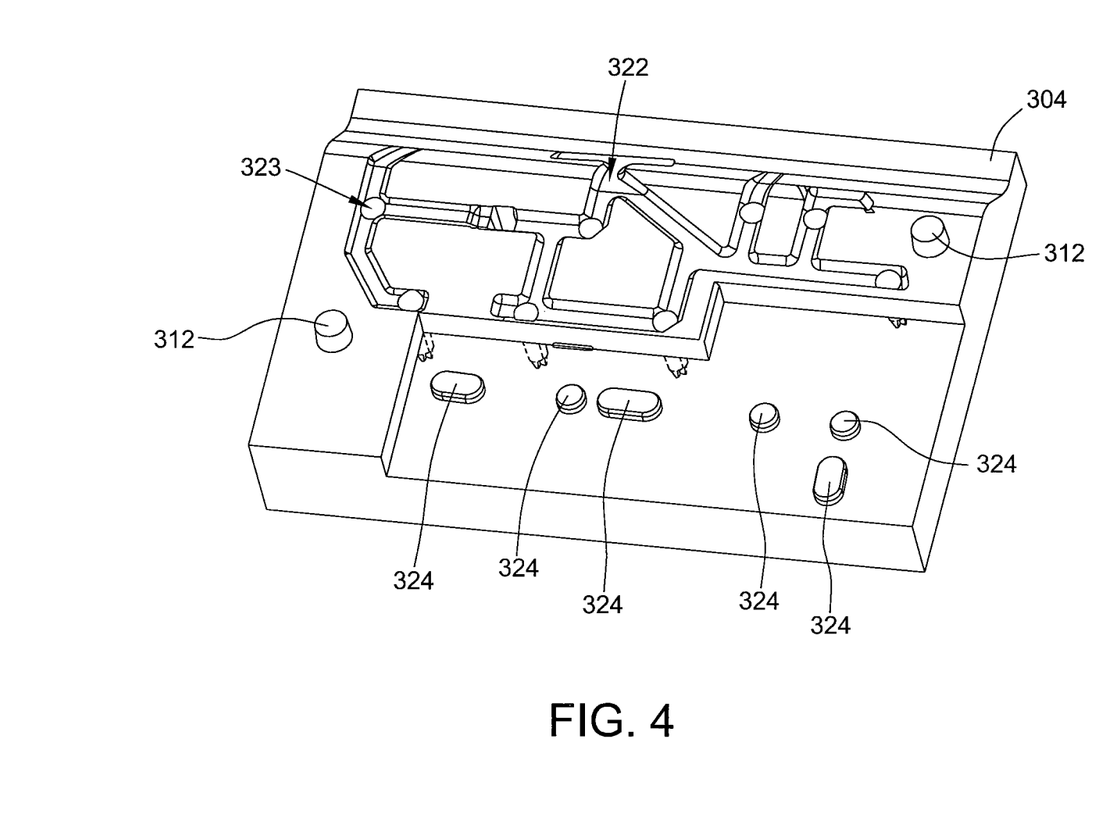
FIG. 4 is a perspective view of a bottom platen that may be used to form the subassembly shown in FIG. 2.

FIG. 3 is a perspective view of a top platen 302, and FIG. 4 is a perspective view of a bottom platen 304. Top and bottom platens 302 and 304 are used to form first and second split webs 208 and 210, respectively. Further, top and bottom platens 302 and 304 are used to form subassembly 200.

As shown in FIGS. 3 and 4, top and bottom platens 302 and 304 are complementary to each other such that that are configured to "fit into" each other. For example, top platen 302 includes two recesses 310 that are sized and oriented to engage two corresponding protrusions 312 in bottom platen 304. To form first split web 208, a thermoplastic, epoxy, and/or thermoset resin may be poured into a first machined area 320 in top platen 302 and cooled. Similarly, to form second split web 210, a thermoplastic, epoxy, and/or thermoset resin may be poured into a second machined area 322 in bottom platen 304 and cooled. Accordingly, first and second split webs 208 and 210 may be created using molding casing or injection molding techniques. During molding, struts 222 are formed by cavities 323 formed in bottom platen 304.

In this embodiment, bottom platen 304 includes a plurality of positioning features 324. Positioning features 324 facilitate locating conductor assembly 204 and antenna assembly 206 during the manufacturing process, as described herein. Positioning features 324 are sized and oriented to engage corresponding positioning feature apertures 326 formed in top platen 302.

Figure 5:
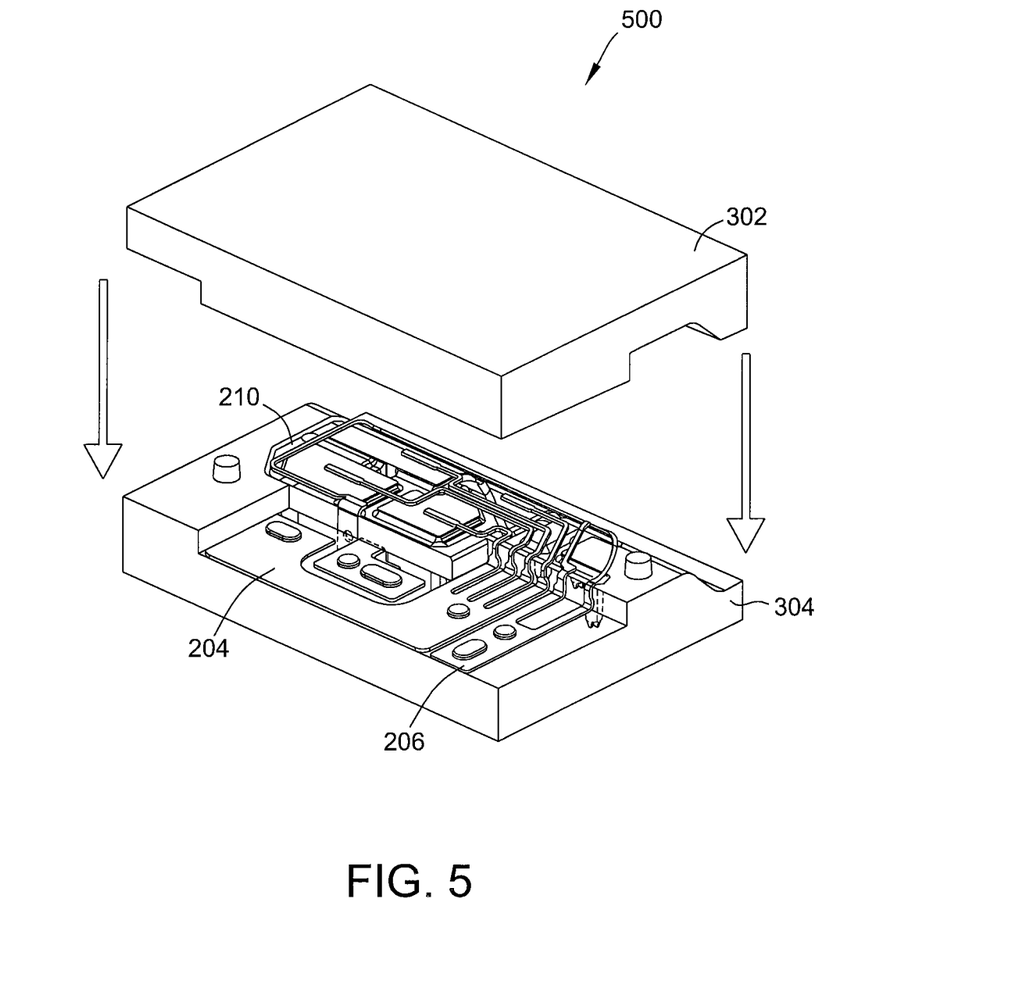
FIGS. 5 and 6 are perspective views of an assembly system that may be used to assemble the subassembly shown in FIG. 2.
Figure 6:
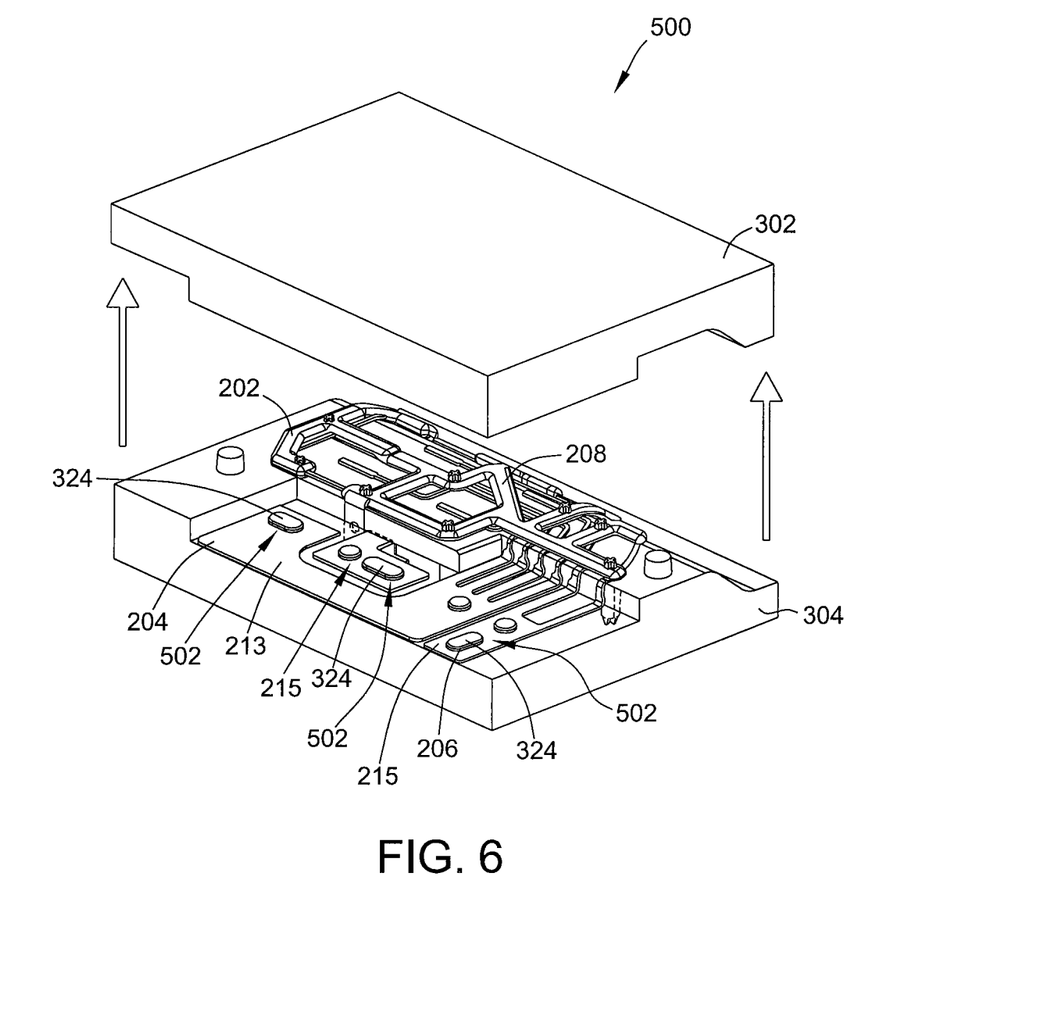

FIGS. 5 and 6 are perspective views of an assembly system 500 that may be used to assemble subassembly 200. Assembly system 500 includes top and bottom platens 302 and 304, first and second split webs 208 and 210, conductor assembly 204, and antenna assembly 206.

Referring now to FIG. 5, to create subassembly 200, first split web 208 (not shown in FIG. 5) is placed in top platen 302, and second split web 210 is placed in bottom platen 304. Placing first and second split webs 208 and 210 may include, for example, forming first and second split webs 208 and 210 using a molding process, as described above.

With second split web 210 placed in bottom platen 304, conductor assembly 204 and antenna assembly 206 are placed in bottom platen 304 on top of second split web 210. As shown in FIG. 6, conductor and antenna base plates 213 and 215 include one or more positioning apertures 502 that facilitate placing conductor assembly 204 and antenna assembly 206 are placed in bottom platen 304. Specifically, positioning features 324 of bottom platen 304 engage corresponding positioning apertures 502 to ensure that conductor assembly 204 and antenna assembly 206 are positioned properly.

To form subassembly 200, top platen 302 (including first split web 208) is lowered relative to bottom platen 304 (including second split web 210, conductor assembly 204, and antenna assembly 206). Top platen 302 engages bottom platen 304, and top and bottom platens 302 and 304 are heated until a predetermined temperature and predetermined pressure are reached.

The predetermined temperature causes the material of first split web 208 and second split web 210 to soften, while the predetermined pressure forces first split web 208 and second split web 210 into contact with one another. This fuses first split web 208 to second split web 210, forming web assembly 202 and forming subassembly 200. To reach the predetermined temperature and predetermined pressures, top and bottom platens 302 and 304 are heated and compressed against one another. Notably, conductor assembly 204 and antenna assembly 206 are positioned between first split web 208 and second split web 210 during the fusing such that portions of conductor assembly 204 and antenna assembly 206 are encapsulated by web assembly 202. Top and bottom platens 302 and 304 may be heated, for example, using internal heating elements incorporated within top and bottom platens 302 and 304 and/or using other techniques.

As shown in FIG. 6, subsequent to fusing and after top and bottom platens 302 and 304 have sufficiently cooled, top and bottom platens 302 and 304 are separated, and the formed subassembly 200 may be removed from bottom platen 304. Subassembly 200 may be used in subsequent manufacturing processes (e.g., a casting and/or molding process) to make a complete IPG header. As shown in FIG. 2, conductor assembly 204 and antenna assembly 206 are positioned between, and thus secured by first split web 208 and second split web 210. Accordingly, web assembly 202 holds electrical conductors 212 and antenna 214 in place during subsequent manufacturing processes.

For example, in one embodiment, subassembly 200 may be used to create a welded subassembly that includes contact rings, connector blocks, and subassembly 200. Specifically, subassembly 200 may be positioned in a welding fixture that facilitates positioning bore and side core pins used to locate the connector blocks. The bore and side core pins may then be introduced into the welding fixture, and respective connector blocks placed on them, such that the connector blocks are positioned to allow attachment of electrical conductors 212. Attachment may be performed by laser welding, resistance welding, conductive epoxy, etc. Once the welded subassembly is created, the welded subassembly may be removed from the welding fixture for manufacturing the complete header assembly.

To create the complete header assembly, the welded subassembly is placed in an injection mold. At appropriate temperatures and pressures (e.g., based on material selection and equipment being used), material is injected into the mold to fully encapsulate the welded subassembly and to take the shape determined by the injection mold. Once cured, the complete header assembly may be assembled onto the IPG. The complete header assembly provides a means for connecting internal components of the IPG to external components that provide sensing and/or deliver associated therapies. The complete header assembly may be used with both thermal setting and thermal cast materials.

Figure 7:
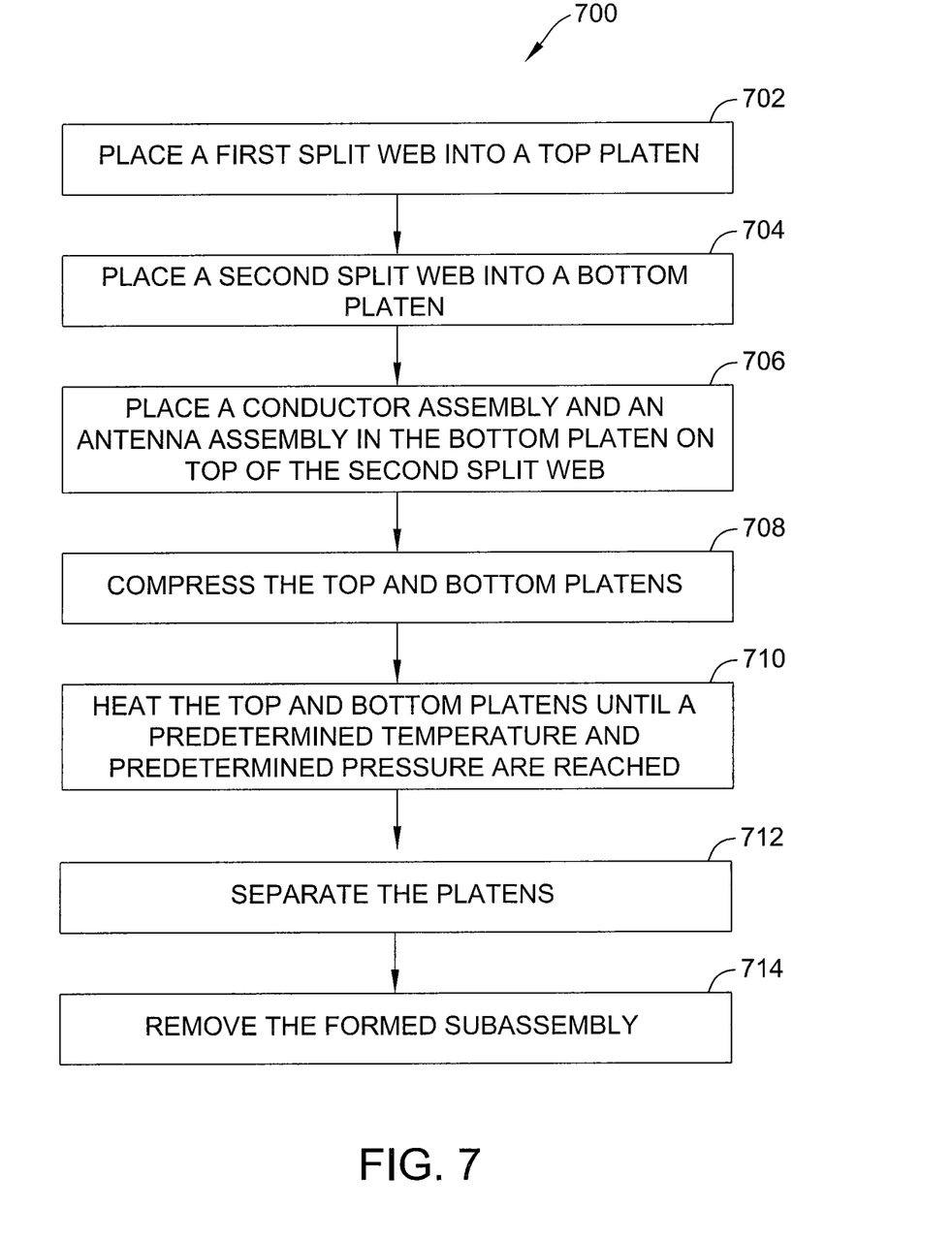
FIG. 7 is a flow chart of one embodiment of a method that may be used to assembly the subassembly shown in FIG. 2.

FIG. 7 is a flow chart of one embodiment of a method 700 for forming a subassembly for use in an IPG header, such as subassembly 200 (shown in FIG. 2). Method 700 includes placing 702 a first split web into a top platen, and placing 704 a second split web into a bottom platen. As explained above, placing 702 a first split web and placing 704 a second split web may include forming the first and second split webs using a molding process. In this embodiment, a conductor assembly and an antenna assembly are placed 706 in bottom platen on top of second split web.

The top platen and the bottom platen are compressed 708 against one another, and heated 710 until a predetermined pressure and predetermined temperature are reached, causing the first and second split webs to fuse together. After cooling, the platens are separated 712, and the formed subassembly is removed 714 from the platens.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable device comprising:
    a header configured to electrically couple the implantable device to a stimulation lead, the header comprising:
    a subassembly comprising:
    a web assembly comprising a first split web fused to a second split web;
    a conductor assembly at least partially encapsulated by and positioned between the first split web and the second split web; and
    an antenna assembly at least partially encapsulated by and positioned between the first split web and the second split web.

2. The implantable device of claim 1, wherein the fused first and second split webs form a web and a plurality of struts that extend from the web in a direction substantially perpendicular to the web.

3. The implantable device of claim 1, wherein the implantable device is configured for use in a deep brain stimulation system.

4. The implantable device of claim 1, wherein the implantable device is configured for use in a cardiac stimulation system.

5. The implantable device of claim 1, wherein the first split web is formed from at least one of a thermoplastic, an epoxy, and/or thermoset resin.

6. The implantable device of claim 1, wherein the second split web is formed from at least one of a thermoplastic, an epoxy, and/or thermoset resin.

* * * * *